United States Patent [19]

Kuiper et al.

[11] Patent Number: 5,782,886
[45] Date of Patent: Jul. 21, 1998

[54] PACEMAKER WITH IMPROVED HYSTERESIS

[75] Inventors: Edoardo C. Kuiper, Duiven; Hendrik Reineman, Zutpen; Johannes S. van der Veen, Dieren, all of Netherlands

[73] Assignee: Vitatron Medical, B.V., Dieren, Netherlands

[21] Appl. No.: 808,314

[22] Filed: Feb. 28, 1997

[51] Int. Cl.$^6$ .................................................. A61N 1/365
[52] U.S. Cl. ........................................................ 607/17
[58] Field of Search ................................. 607/9, 17, 25

[56] References Cited

U.S. PATENT DOCUMENTS

| | | | |
|---|---|---|---|
| 3,656,487 | 4/1972 | Gobeli . | |
| 4,097,766 | 6/1978 | Renirie | 307/220 |
| 4,169,480 | 10/1979 | Digby et al. | 128/419 PG |
| 4,363,325 | 12/1982 | Roline et al. . | |
| 4,856,523 | 8/1989 | Sholder et al. . | |
| 5,016,630 | 5/1991 | Moberg . | |
| 5,284,491 | 2/1994 | Sutton et al. | 607/17 |
| 5,391,189 | 2/1995 | van Krieken et al. | 607/17 |
| 5,454,836 | 10/1995 | van der Veen et al. | 607/17 |
| 5,501,701 | 3/1996 | Markowitz et al. | 607/9 |
| 5,522,859 | 6/1996 | Stroebel et al. | 607/19 |
| 5,540,728 | 7/1996 | Shelton et al. | 607/23 |
| 5,674,257 | 10/1997 | Stroebel et al. | 607/17 |
| 5,676,686 | 10/1997 | Jensen et al. | 607/9 |

*Primary Examiner*—Jeffrey R. Jastrzab
*Attorney, Agent, or Firm*—Woodcock Washburn Kurtz Mackiewicz & Norris, LLP

[57] ABSTRACT

An implantable pacemaker system is provided with a conditional hysteresis feature, whereby a hysteresis value is added to the pacing escape interval only when the prior spontaneous rate corresponded to a rate below the top of a predetermined hysteresis band. This feature limits the lengthening of the escape interval when there are sudden drops in the natural rate thereby avoiding excessive changes in rate. In a preferred embodiment, the pacemaker defines a hysteresis band around a given pacing rate, e.g., lower rate limit, the band having an upper hysteresis limit and a lower hysteresis limit. No hysteresis lengthening of the escape interval is utilized for spontaneous heartbeats having rates above the upper hysteresis limit; for spontaneous heartbeats having rates between the lower rate limit and the upper hysteresis limit, an escape interval is set to have a value corresponding to a rate between the pacing limit and the lower rate limit of the hysteresis band which is, e.g., 0–30 bpm below the lower rate limit; and for a sensed spontaneous rate below the lower rate limit, a hysteresis escape interval corresponding to the lower hysteresis limit is established. In the preferred embodiment, sensed heartbeats having a prior rate between the lower rate limit and the upper hysteresis limit cause an escape interval which is lengthened beyond the LRL escape interval by an amount which varies linearly with the differential between the upper hysteresis rate limit and the spontaneous rate.

26 Claims, 6 Drawing Sheets

PACEMAKER WITH IMPROVED HYSTERESIS

FIELD OF THE INVENTION

This invention relates to cardiac pacemakers and, more particularly, pacemakers which incorporate rate hysteresis to enable sensing spontaneous heartbeats which may occur at rates within a hysteresis band below the pacing lower rate limit.

BACKGROUND OF THE INVENTION

The feature of rate hysteresis is known in cardiac pacemakers. For example, most single chamber VVI pacemakers provide a form of rate hysteresis, which is designed to prolong the pacing escape interval after a spontaneous event. For example, a pacemaker may be programmed to pace at 70 beats per minute (bpm), but as long as spontaneous beats are being sensed at rates above 70 bpm, the escape interval may be set to correspond to a lower rate, e.g., 60–65 bpm. The advantage of hysteresis is that it enables the pacemaker to follow a mildly lower spontaneous rhythm, i.e., one which might be just slightly below the lower rate limit (LRL) used for pacing but still at a high enough rate that it is not necessary to override these spontaneous heartbeats with pacing. This has the advantage of extending pacemaker longevity, because the pacemaker paces less often. Further, as long as a spontaneous rhythm is enabled, the heart has its natural AV synchrony, providing the most optimal contraction sequence of the ventricle following the atrial contraction.

A problem with hysteresis generally in cardiac pacemakers is that it can lead to excessive changes in rate. Usually, hysteresis is active regardless of the spontaneous rate prior to a sudden rate drop. Whether the spontaneous rate is close to the lower rate limit or far exceeds it, the pacemaker shifts to pace at the relatively low hysteresis rate at the first absence of a spontaneous beat. Thus, if the spontaneous rate is relatively high, e.g., 90 bpm compared to an LRL of about 70 bpm, this results in a large drop in heart rate when the pacemaker times out a hysteresis escape interval corresponding to a rate in the range of 60–65 bpm. Such a large drop in heart rate can have possible hemodynamic consequences, and the patient may experience a palpitation because of the sudden change in ventricular filling.

There have been a number of different arrangements designed to enhance the hysteresis feature in cardiac pacemakers. For example, U.S. Pat. No. 5,016,630 discloses a rate responsive pacemaker that varies the pacing rate, and provides a hysteresis interval which varies as a function of the escape interval corresponding to the dynamic pacing rate. In another arrangement, referred to as rate drop response, the variation of escape interval after hysteresis pacing is defined by the rate of change in the spontaneous intervals before the hysteresis pacing. See U.S. Pat. No. 5,284,491. However, these designs do not address the need for preventing large rate drops when the spontaneous rate is high before a sudden rate decrease.

SUMMARY OF THE INVENTION

It is an object of this invention to provide a cardiac pacemaker with rate hysteresis, and wherein the hysteresis extension of the pacing escape interval is utilized only if the prior spontaneous rate is found to be sufficiently close to the pacing rate so that the hysteresis extension does not result in an excessive rate change. In the context of this invention, the spontaneous rate can be determined as the rate corresponding to the last interval, or it can be calculated as a moving rate, e.g., the average over the last N intervals. The objective is met by conditioning hysteresis on the rate before the rate drop, i.e., hysteresis is conditional and is only allowed when the spontaneous rate is relatively close to the pacing rate limit.

In accordance with the above objective, there is provided an implantable pacemaker system and method for pacing a patient, having a hysteresis feature for lengthening the escape interval following a spontaneous heartbeat, but enabling the hysteresis only in response to sensed heartbeats having rates within a predetermined band above the pacing rate (e.g., LRL). When the spontaneous rate is above the hysteresis enabling band, the escape interval is set at the LRL pacing limit; when the spontaneous rate is found to be above LRL but within the hysteresis enabling band, then the escape interval is set to correspond to a rate between the pacing limit and a lower hysteresis limit (LHL), the escape interval being determined as a function of the spontaneous rate. When the spontaneous rate, determined either as the instantaneous rate of the last beat or as an average rate, is below LRL, the escape interval is set to correspond to LHL.

In the practice of this invention, the pacemaker system can be either ventricular or atrial single chamber, or can be a dual chamber system.

DESCRIPTION OF THE PREFERRED EMBODIMENTS

Figure 1:
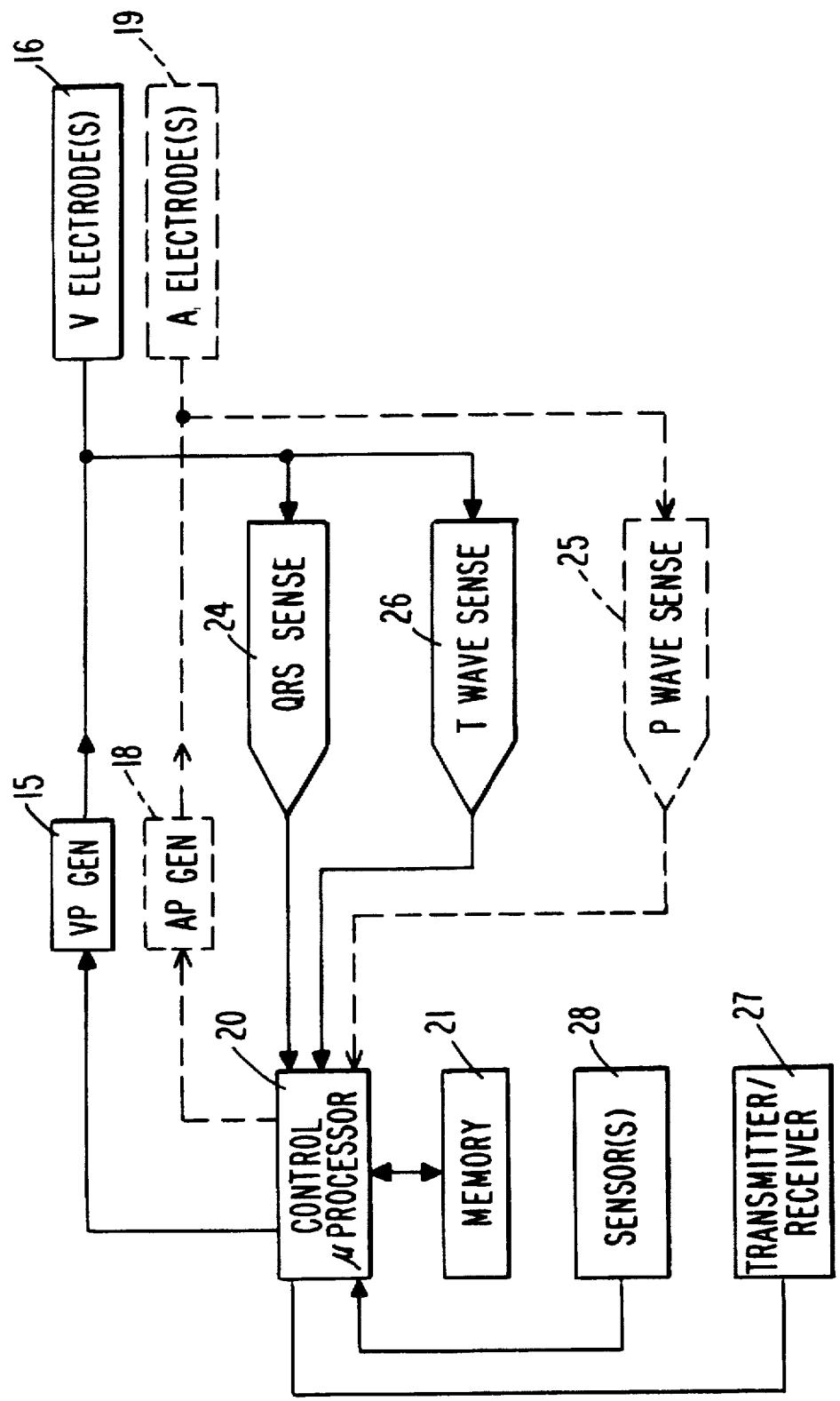
FIG. 1 is a block diagram showing the standard components of a single chamber pacemaker as used in the practice of this invention.

Referring now to FIG. 1, there is shown a simplified block diagram of the primary components of a pacemaker as used in the system and method of this invention. While this invention is illustrated as a single chamber ventricular pacemaker, it is to be understood that it could be an atrial chamber pacemaker or a dual chamber pacemaker; in FIG. 1, the portion unique to such an atrial embodiment is shown in dashed lines. A ventricular pace generator is illustrated at 15 for generating and delivering ventricular pace pulses under control of control unit 20, in a known fashion. The ventricular pace pulses are delivered to one or more ventricular electrodes illustrated at 16. Alternately, as shown in dashed lines, an atrial pace generator is illustrated at 18, which generates atrial pace pulses under control of unit 20 and delivers the atrial pace pulses to one or more atrial electrodes as illustrated at 19. Sense signals from the ventricular electrode or electrodes are connected to QRS sense amplifier 24 and T-wave sense amplifier 26, the outputs of which are inputted to control block 20 for processing. Although not shown, it is understood that by those of skill in the pacemaker art that the input amplifiers 24, 26 are controlled in terms of sensitivity and timing by control unit 20. For an AAI or AAT pacemaker, signals detected in the atrium by electrodes 19 are delivered to P-wave sense amplifier 25 (as shown in dashed lines), the output of which is connected through to control 20.

Control block 20 suitably incorporates a microprocessor with associated software, the software being stored in memory 21, as indicated. Memory 21 may contain RAM and ROM, and the assignment of pacemaker functions can be divided between hardware and software in any desired manner. In the preferred embodiment of this invention, the escape interval algorithms are suitably carried out under software control. One or more sensors 28 may optionally be provided to continuously detect rate-indicating parameters, the parameter signals being inputted to control block 20 to provide rate responsive control, in a known manner. Alternately, a rate responsive parameter may be QT interval, which is determined by control 20 by timing the duration between a delivered stimulus (VP) and the following T wave. As illustrated at 27, the pacemaker suitably has a transmitter/receiver for receiving programmer communications from an external programmer, and for transmitting collected data back to a transmitter, in a known fashion.

As used herein, the following definitions apply:

| Abbreviation | Definition |
| --- | --- |
| VP | ventricular pace |
| VS | ventricular sense |
| Esc_int | escape interval |
| LRL | lower rate limit; normal pacing rate |
| LRL_int | escape interval corresponding to LRL |
| R | spontaneous rate |
| LHL | lower limit of hysteresis band |
| LHL_int | escape interval corresponding to LHL |
| UHL | upper limit of hysteresis band, e.g., LRL + 15 |
| UHL_int | escape interval corresponding to UHL |
| Hyst | LRL − LHL |
| Hyst (R) | hysteresis rate between LRL and LHL, calculated following LRL ≦ R ≦ UHL |
| Hyst_int (R) | escape interval corresponding to Hyst (R) |
| DPL | dynamic pacing limit |
| DPL_int | escape interval corresponding to dynamic pacing limit |

Figure 2:
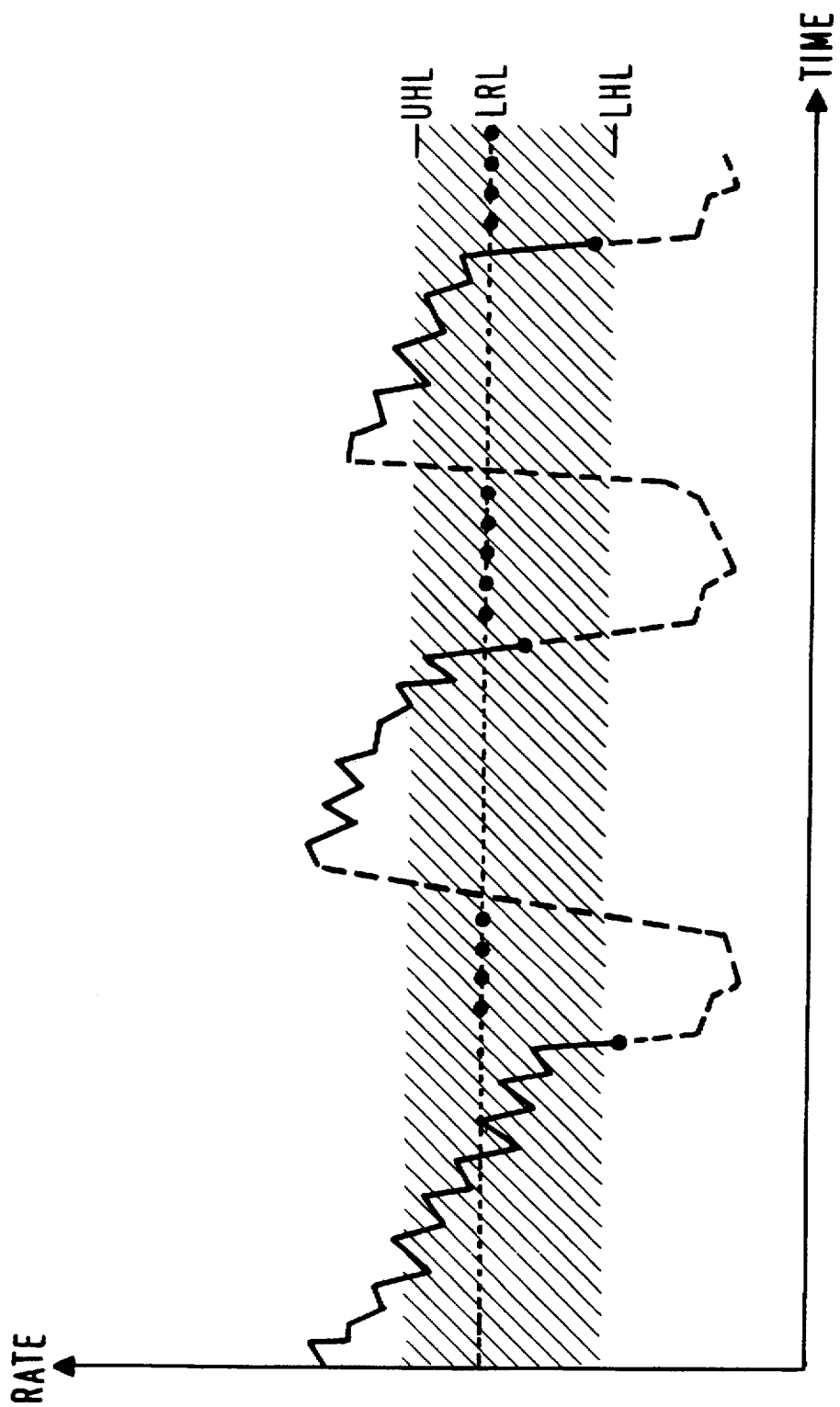
FIG. 2 is a timing diagram illustrating the operation of this invention, showing the hysteresis setting following different spontaneous rates relative to the pacing limit (LRL).

Referring now to FIG. 2, there is shown a timing diagram that illustrates the primary features of the preferred embodiment of conditional hysteresis as used in this invention.

The timing diagram of FIG. 2 assumes that the pacing rate is fixed at a lower rate limit (LRL); an embodiment where the pacing rate is dynamic is discussed below. The rate indicated as the upper hysteresis limit (UHL), suitably LRL+15 bpm, defines the rate below which hysteresis is enabled. Thus, for spontaneous beats at or below UHL, a hysteresis escape interval will be set. The actual hysteresis rates be between LRL and LHL, where LHL equal LRL−Hyst. Hyst is a programmable value, e.g., 0–30 bpm, limited so that LHL has a minimum rate of e.g., 40 bpm. The conditional hysteresis of this invention is active in the band from UHL down to LHL, to provide an extension of the escape interval after a spontaneous event.

Still referring to FIG. 2, it is seen that if a patient's spontaneous rate is at or below LRL and then suddenly drops, the pacemaker delivers the first stimulus at LRL−Hyst, or LHL, and then returns to pacing at LRL. As seen at the left of the timing diagram, the spontaneous rate is proceeding downward cycle by cycle from a value above UHL. It continues to drop at a moderate rate down through LRL, and then at a point below LRL but above LHL, the spontaneous rate drops quickly. As indicated, in response to this situation, a pace pulse is delivered at an escape interval corresponding to LHL, i.e., Esc_int=LHL_int. Although not shown, two or more beats can be delivered at LHL as an option. Following this, pacing is carried out at LRL for four cycles until the spontaneous rate rises above LRL. In the next sequence, indicated in the center of the timing diagram, the spontaneous rate again varies from a value above UHL down into the hysteresis band between LRL and UHL. At this point, when the rate suddenly stops, the pacemaker starts pacing at an escape rate between LRL and LHL. As indicated here, the pacing rate is just below, or relatively close to LRL. Following this, five paces are shown being delivered at LRL, and then the rate again rises above UHL. This time, the rate proceeds down closer to LRL, and upon a sudden drop of the rate, a beat is delivered at an escape interval which is close to LHL. The escape interval rate which is set following spontaneous beats between LRL and UHL is dependent upon where the patient's spontaneous rate lies prior to pacing. For example, if the spontaneous rate is in the top part of the hysteresis band, just below UHL, the escape interval is set to be slightly below LRL; if the spontaneous rate just exceeds LRL, the escape interval is set just above LHL.

In a preferred embodiment, the hysteresis escape rate varies linearly with respect to where R lies between LRL and UHL. This rate, referred to as hyst (R) may be expressed as follows:

$$Hyst(R) = LRL - \frac{(UHL - R)}{UHL - LRL} \cdot Hyst$$

Thus, for $Hyst = LRL - LHL = 30$, and $$UHL - LRL = 15, Hyst(R) = LRL - (UHL - R) \cdot 2$$

Figure 3:
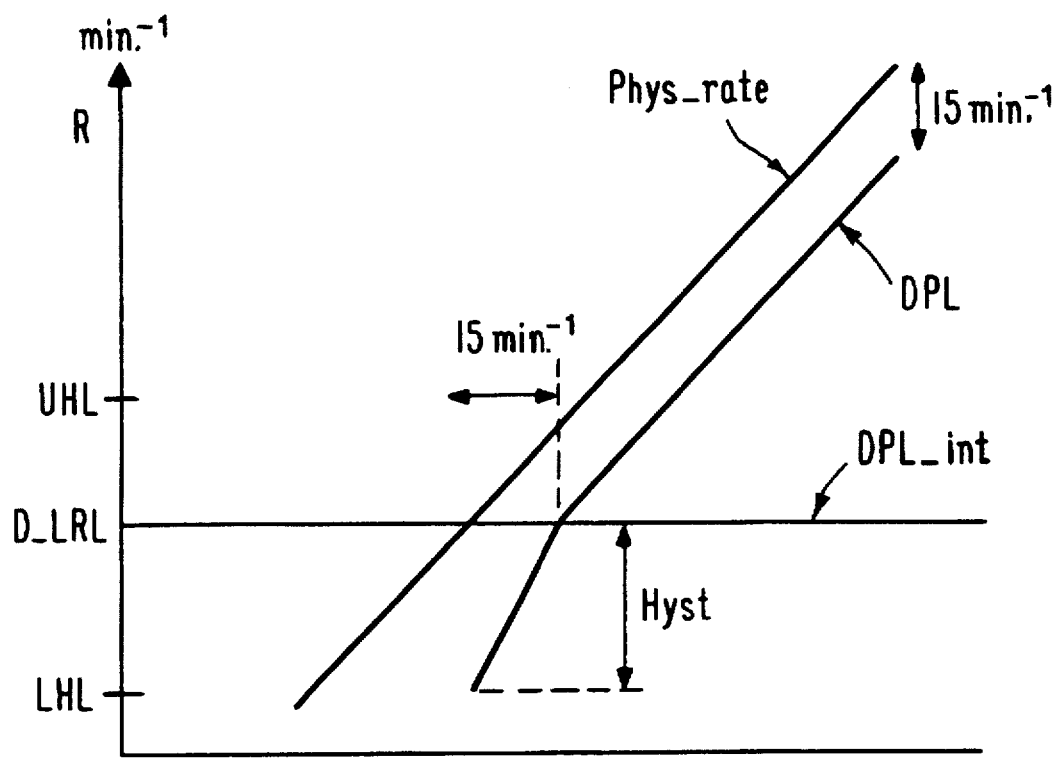
FIG. 3 is a graph showing the relationship between spontaneous rate and pacing rate, illustrating the conditional hysteresis.

Referring now to FIG. 3, there is shown a rate diagram illustrating single chamber hysteresis for a daytime setting of LRL, D_LRL. This diagram represents a fixed pacing rate, LRL, having an escape interval LRL_int; as well as a dynamic pacing rate DPL, having an escape interval DPL_int. In either event, hysteresis is not invoked until the spontaneous rate drops to within 15 bpm of the LRL value. For lower rates, it is seen that the programmed hysteresis increment drops linearly to the LHL value. It is to be noted that for a pacemaker that switches to a lower nighttime setting of LRL, the hysteresis slope below LRL can be adjusted accordingly.

Figure 4:
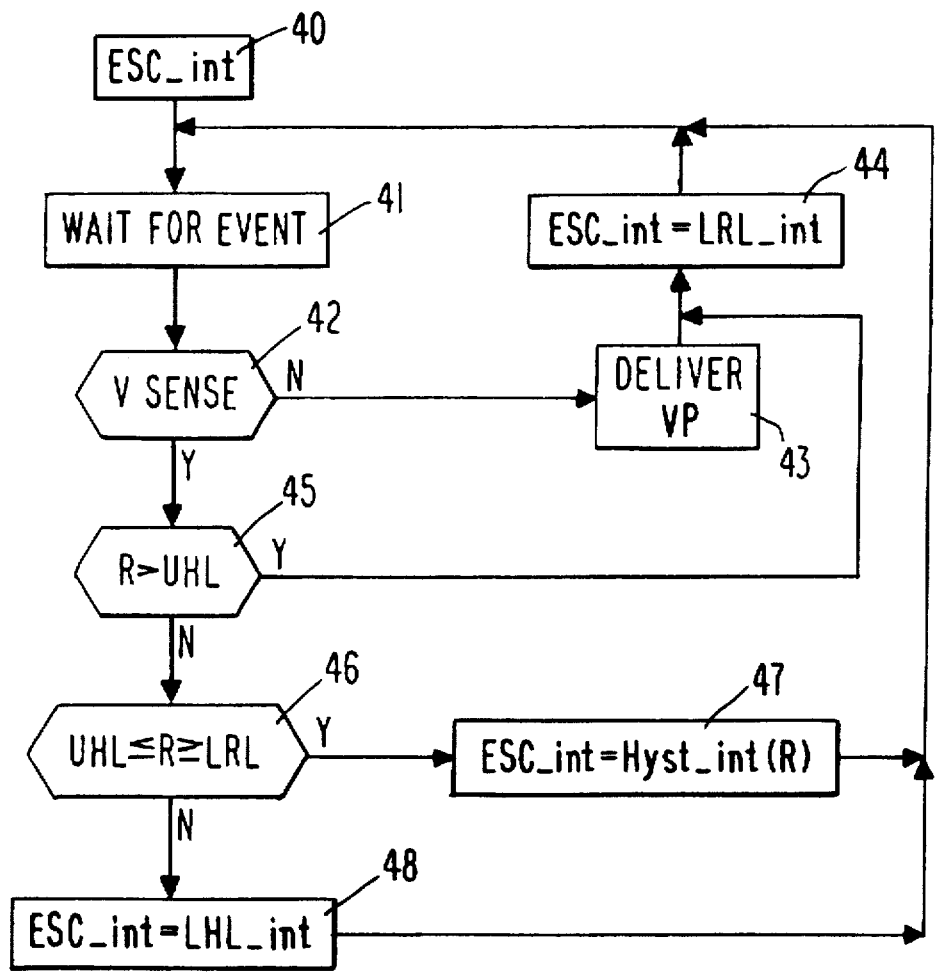
FIG. 4 is a flow diagram showing the decisions taken in carrying out the conditional hysteresis feature illustrated in the timing diagram of FIG. 2.

Referring now to FIG. 4, there is shown a flow diagram of the preferred embodiment of this invention, where Esc_int, except for hysteresis, is fixed at LRL_int. It is to be understood that while the conditional hysteresis is illustrated for a ventricular pacemaker, it is equally applicable to pacemakers operating in the VVI, AAI, VVT, AAT, DDI and DDD modes. Starting at block 40, the escape interval Esc_int is initially set. AT 41, the pacemaker waits for an event, and 42 it is determined whether the event is a V-sense. If no, meaning that the escape interval timed out, at 43 the pacemaker delivers a ventricular pace pulse. Following this, at 44 Esc_int is set equal to LRL_int, and the pacemaker goes back to 41 and waits for the next event.

Returning to 42, if there has been a V-sense, the routine goes to 45 and determines whether the spontaneous rate R is greater than the upper hysteresis limit UHL. If yes, this means that no hysteresis is to be enabled, and the routine branches to block 44 and sets the escape interval to correspond to LRL. However, if at 45 the answer is no, then the routine goes to 46 and determines whether the spontaneous rate is in the hysteresis enabling band between LRL and UHL. If yes, at 47, Esc_int is calculated as Hyst_int(R), as discussed above. If no, meaning that the spontaneous rate has dropped below LRL, then at 48 the escape interval is set equal to LHL_int. Note that if a pace pulse is delivered at LHL, then the next escape interval is set at LRL_int, such that pacing continues at LRL.

Figure 5:
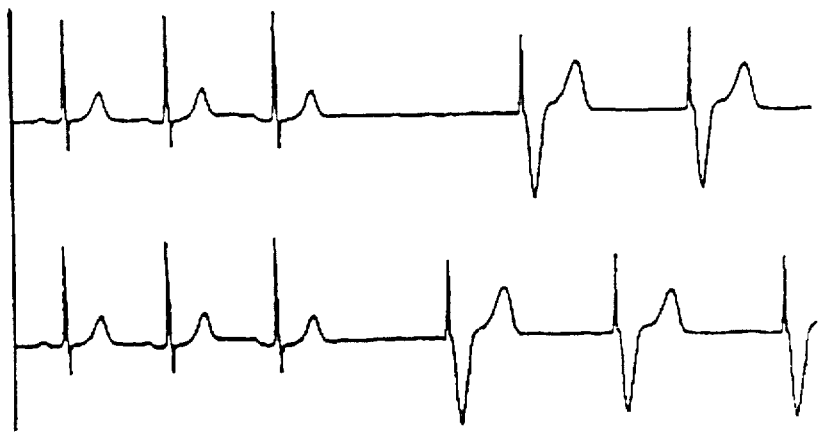
FIG. 5 is an illustration of EKGs illustrating the difference between a pacemaker with and without the conditional hysteresis feature of this invention.

The result of the conditional hysteresis as illustrated in FIGS. 2 and 4 is seen in the EKG diagrams of FIG. 5. The top EKG shows a standard hysteresis pacemaker, where a high spontaneous rate suddenly drops. At this point, the pacemaker starts pacing at the hysteresis rate, and continues pacing at the lower limit, resulting in a large pause before pacing starts. It is this extended pause which this invention modifies, thus providing the benefit. The EKG on the bottom shows the effect of the conditional hysteresis. Here, where the spontaneous rate suddenly drops, the pacemaker starts pacing at the lower rate limit, preventing the large or extended pause.

Figure 6A:
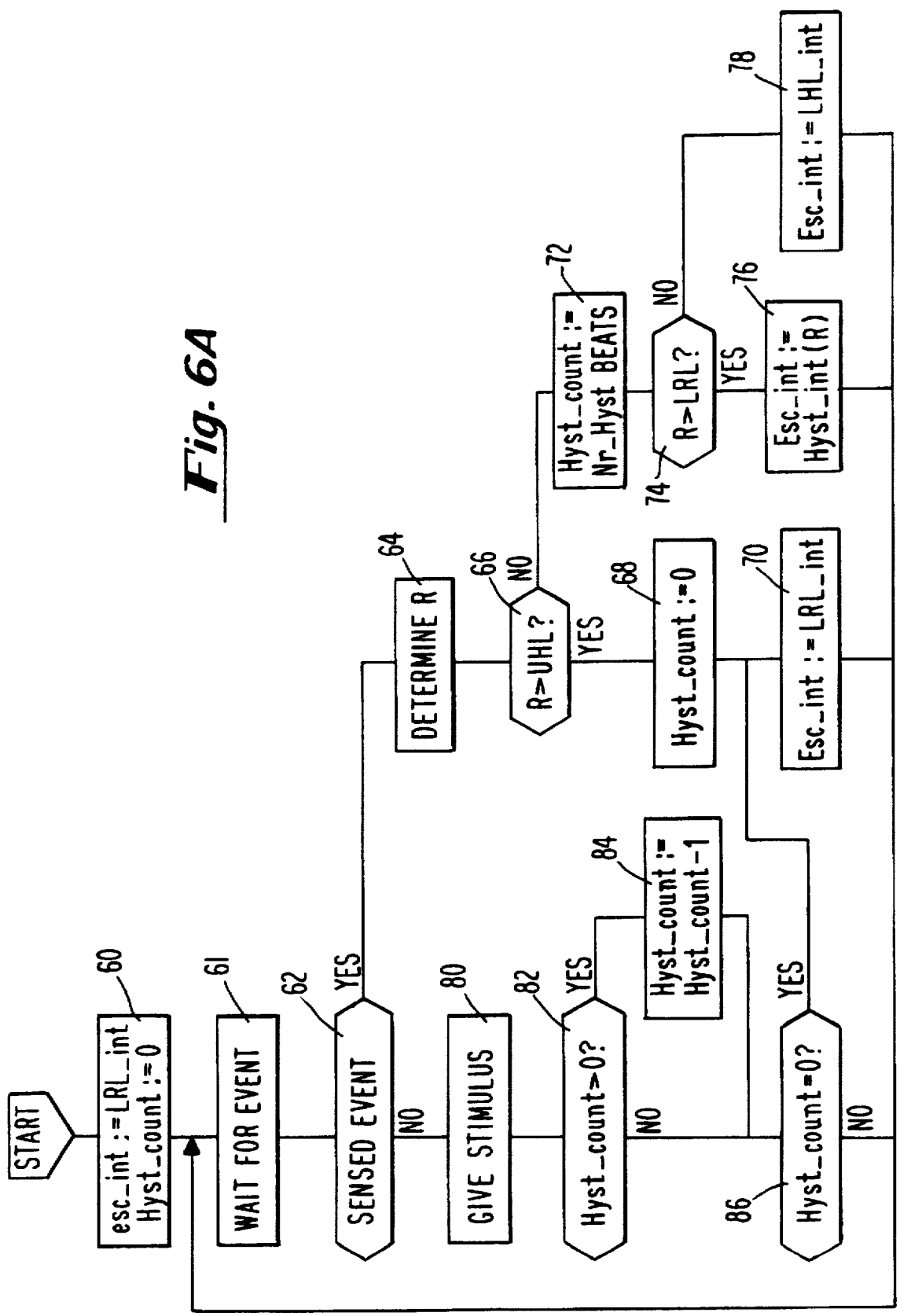
FIG. 6A is a flow diagram of an alternate embodiment of this invention, providing for pacing for two or more beats at the hysteresis rate after pacing has taken over from a spontaneous rhythm.

Referring now to FIG. 6A, there is illustrated an alternate embodiment which permits pacing at the hysteresis rate more than just once, e.g., a programmable number of beats are delivered at Hyst(R) before the pacemaker reverts to pacing at LRL. The embodiment of FIG. 6A is a special case, and it is to be understood that one or more follow-up pace pulses can be delivered at rates between LRL and LHL other than at Hyst(R), in accordance with a programmed pattern. Thus, pacing a programmable number of beats at one given rate is exemplary.

As indicated at block 60, Esc_int is set equal to LRL_int, and the variable Hyst_count is set equal to zero. At 61, the pacemaker waits for the next event. At 62, it is determined whether the event has been a sense, i.e., whether an atrial or ventricular contraction has been sensed. If yes, the routine branches to block 64 and determines the rate R. As discussed above, this may be the rate corresponding to the last interval, or may be a running average of recent spontaneous heartbeats. At 66, it is determined whether R is greater than UHL. If yes, at 68 the variable Hyst-count is set equal to zero, and at 70 Esc_int is set equal to LRL_int. However, if at 66 R is determined not to be greater than UHL, such that the spontaneous rate is within the hysteresis band, then at 72 Hyst_count is set equal to NR_Hyst_beats, which may be a programmable number, e.g., 2, 3, etc. Note that if this number is set equal to one, it is the same as the embodiment of FIG. 4. Then, at 74 it is determined whether R is greater than LRL. If yes, at 76 Esc_int is set equal to Hyst_int (R). However, if R is not greater than LRL, then at 78 Esc_int is set equal to LHL_int.

Returning to block 62, if the event is not a sense, this means that the escape interval has timed out. The routine goes to 80 and delivers a stimulus pulse. Then, at 82, it is determined whether Hyst_count is greater than zero. If yes, then at 84 this variable is set equal to Hyst_count-1. At 86, it is determined whether the variable Hyst_count is equal to zero. If yes, the routine goes to 70 and sets Esc_int equal to LRL_int; if no, the routine exits directly back to block 61. It is thus seen that if the spontaneous rate is detected to be above LRL but below UHL, whenever the escape interval times out, two or more beats will be delivered at the hysteresis rate before the escape interval goes back to LRL_int. This permits the greater opportunity for an underlying spontaneous rhythm with a rate greater than Hyst(R) to be sensed.

Figure 6B:
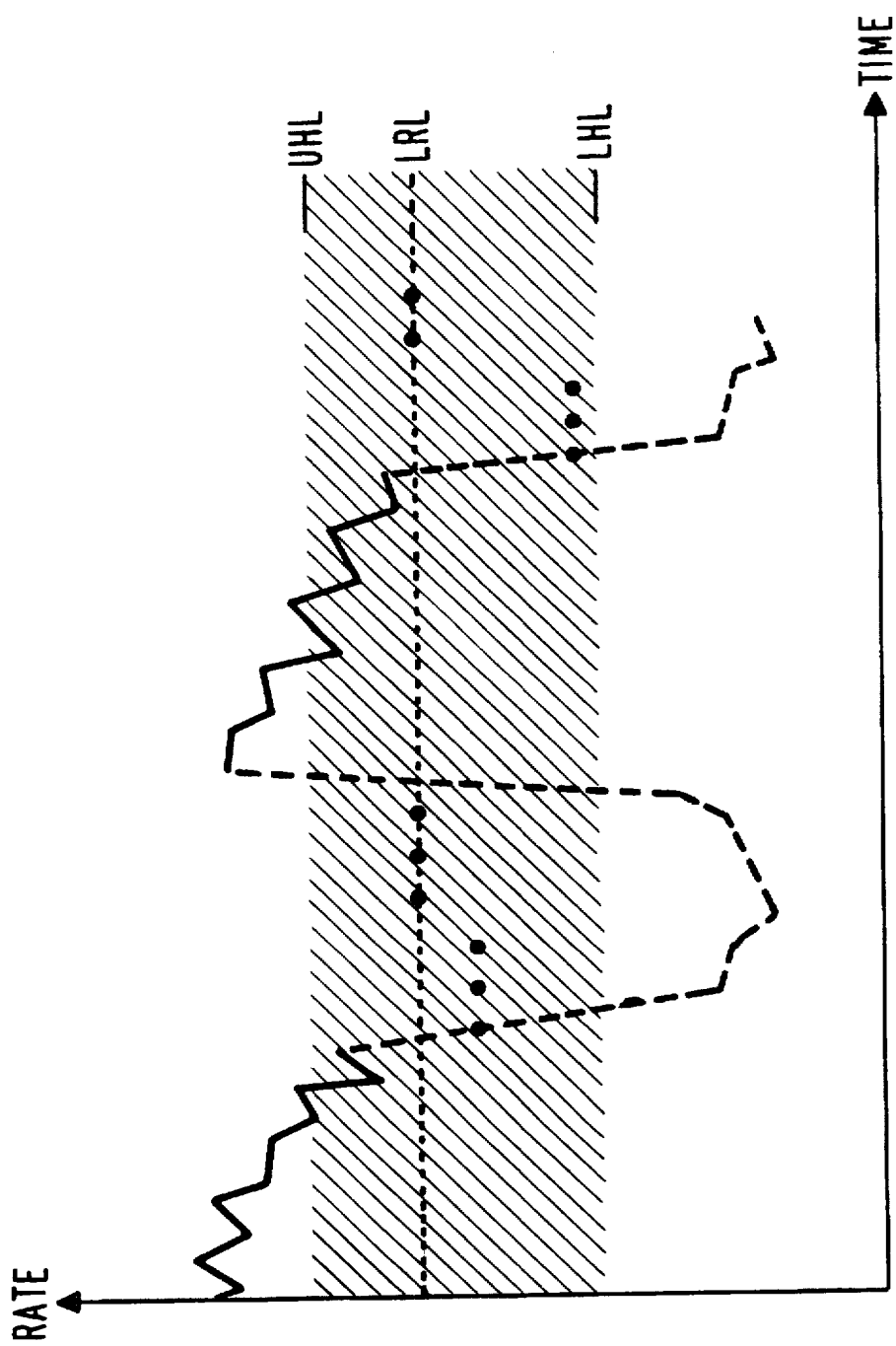
FIG. 6B is a timing diagram illustrating the embodiment of FIG. 6A, where two additional pace pulses are delivered at the hysteresis rate.

Referring to FIG. 6B, there is a shown a timing diagram for the embodiment of FIG. 6A, wherein NR_Hyst_beats is set equal to 3. As can be seen, each time the spontaneous beat is lost, and the prior spontaneous rate had been between UHL and LRL, three pace pulses are delivered at Hyst(R). Following the three pace pulses delivered at the hysteresis rate, and in the absence of the re-occurrence of a spontaneous rate above LRL, pacing is continued at LRL.

It is to be understood that the invention can be incorporated into different pacing systems. Thus, LRL can be varied to track the natural, or spontaneous rate, in accordance with the known flywheel arrangement. Alternately, LRL may be varied by input from one or more rate responsive sensors.

As used in defining this invention, rate can be determined by any one of several techniques, including determining the rate that corresponds to the interval concluded by a sensed heartbeat, by determining a running average, or a physiological rate. The terms "a measure of rate" and a "corresponding spontaneous rate" embrace the above meanings. The phrase "timing out" an escape interval is used in the normal sense, i.e., after a pace or sense event, the escape interval timer is set, and proceeds to time out if there is no intervening sensed beat.

We claim:

1. An implantable pacemaker system for pacing a patient, comprising:

pace means for generating and delivering pace pulses to said patient's heart;

sense means for sensing natural heartbeats from said patient's heart and rate means for determining a measure of the rate (R) of said sensed heartbeats;

escape means for setting and timing out an escape interval following each delivered pace pulse and each sensed heartbeat, and for controlling said pace means to deliver a pace pulse when a said escape interval times out without an intervening sensed heartbeat;

LRL means for normally setting said escape interval to a value corresponding to a lower rate limit (LRL);

band means for defining a hysteresis band with an upper hysteresis rate limit (UHL) at a rate greater than said LRL and a lower hysteresis rate limit (LHL) at a rate lower than said LRL; and hysteresis means operative in response to a sensed heartbeat having a rate (R) between said LRL and said UHL for adjusting said escape interval to a hysteresis value corresponding to a rate within the range defined by said LRL and said LHL.

2. The system as described in claim 1, wherein said hysteresis means comprises means for determining said hysteresis value as a function of R.

3. The system as described in claim 2, wherein said hysteresis means comprises means for determining a hysteresis rate portion which varies linearly with the difference between UHL and R, and for adjusting said escape interval to a conditional value that corresponds to a rate of LRL minus said hysteresis rate portion.

4. The system as described in claim 3, comprising means for setting said escape interval to said conditional value for a predetermined number of beats in the absence of sensed natural heartbeats.

5. The system as described in claim 1, comprising a second hysteresis means operative in response to a sensed beat having a rate between said LRL and said LHL to set the escape interval to an interval corresponding to LHL for at least one beat and to thereafter set said escape interval to an interval corresponding to LRL until a next sensed natural beat.

6. The system as described in claim 1, wherein said rate means comprises average means for determining a running average rate of sensed natural beats.

7. The system as described in claim 1, wherein said rate means comprises means for determining the rate of the last two patient heartbeats.

8. The system as described in claim 1, comprising high rate means for determining when sensed beats have spontaneous rates above said UHL, and for setting the escape interval to correspond to LRL whenever a said rate is above UHL.

9. The system as described in claim 1, comprising UHL means for setting said UHL at LRL plus a fixed value.

10. The system as described in claim 1, comprising LHL means for setting said LHL to a programmable minimum rate.

11. The system as described in claim 1, wherein said band means comprises means for programming the differential between LRL and LHL.

12. The system as described in claim 1, comprising repeat means for controlling said pace means to generate and deliver a predetermined number of pace pulses at an escape interval having said hysteresis value, in the absence of natural heartbeats after a last sensed beat having a rate between UHL and LRL.

13. The system as described in claim 12, wherein said repeat means comprises program means for setting said predetermined number to a programmed value.

14. An implantable pacemaker system, comprising generator means for generating and delivering pace pulses to a patient, sense means for sensing spontaneous heartbeats of said patient, rate means for determining a measure of the rate of sensed spontaneous beats, escape means for setting an escape interval after each delivered pace pulse and each sensed heartbeat and for timing out each said escape interval until a next event, control means for controlling said generator means to generate and deliver a pace pulse whenever a said escape interval times out, said escape means having means operative after a sensed beat for setting the next escape interval as the sum of a first escape interval portion and a hysteresis interval portion, and hysteresis means for determining said hysteresis interval portion to be zero whenever said spontaneous beat rate is above a predetermined rate (UHL) and to be a function of said rate when said rate is below said UHL.

15. The system as described in claim 14, wherein said escape means comprises LRL means for setting a lower rate pacing limit and for setting said escape interval to correspond to said LRL after a sensed beat at a rate above said UHL, and means operative after a delivered pace pulse at timeout of an escape interval with a nonzero hysteresis portion for setting the next escape interval to correspond to said LRL.

16. The pacemaker system as described in claim 15, wherein said escape means has means for setting said first portion to correspond to said LRL and for setting said hysteresis portion to a value proportional to said UHL minus said rate measure.

17. The system as described in claim 16, wherein said rate means comprises means for determining the rate corresponding to the pacemaker cycle ended by the last sensed spontaneous heartbeat.

18. The system as described in claim 16, wherein said rate means comprises means for determining a running average of the rate of a plurality of sensed spontaneous beats.

19. The system as described in claim 14, comprising means operative after timeout of an escape interval having a non-zero hysteresis portion for setting the next escape interval to correspond to a predetermined lower rate limit.

20. The system as described in claim 14, comprising means responsive to delivery of a pace pulse upon timeout of an escape interval having a non-zero hysteresis portion for thereafter setting the escape interval to substantially the same value for a predetermined number of intervals.

21. A method of setting the escape interval of a cardiac pacemaker to conditionally include a hysteresis portion, comprising:

determining a pacing rate, an upper hysteresis rate limit above said determined pacing rate and a lower hysteresis limit below said determined pacing rate, sensing heartbeats and determining a spontaneous rate corresponding to each said sensed heartbeat, determining when spontaneous rate is between said upper hysteresis rate limit and said determined pacing rate, and responding to a heartbeat having a corresponding spontaneous rate between said upper hysteresis rate limit and said determined pacing rate by setting the next escape interval to have a first value corresponding to said determined pacing rate and a second hysteresis portion which is a variable function of said spontaneous rate.

22. The method as described in claim 21, comprising adding said hysteresis portion to the escape interval only following sensed spontaneous heartbeats between said upper hysteresis limit and said determined pacing rate.

23. The method as described in claim 21, comprising setting said upper hysteresis limit at a programmable UHL value, setting said determined pacing rate at a programmed LRL value, and setting said lower hysteresis limit at a programmed LHL value.

24. The method as described in claim 23, comprising varying said LRL to track the spontaneous rate in a flywheel manner.

25. The method as described in claim 23, comprising varying said LRL in accordance with at least one sensed rate-indicating parameter.

26. The method as described in claim 23, comprising setting the next escape interval to correspond to said LHL after a sensed beat having a rate between said LRL and said LHL.

* * * * *